(12) United States Patent
Wustefeld et al.

(10) Patent No.: US 8,873,058 B2
(45) Date of Patent: Oct. 28, 2014

(54) OPTICAL SENSOR

(71) Applicant: Sick AG, Waldkirch/Breisgau (DE)

(72) Inventors: Martin Wustefeld, Sexau (DE); Robert Bauer, Emmendingen (DE)

(73) Assignee: Sick AG, Waldkirch/Breisgau (DE)

( * ) Notice: Subject to any disclaimer, the term of this patent is extended or adjusted under 35 U.S.C. 154(b) by 45 days.

(21) Appl. No.: 13/773,803

(22) Filed: Feb. 22, 2013

(65) Prior Publication Data

US 2013/0222805 A1 Aug. 29, 2013

(30) Foreign Application Priority Data

Feb. 24, 2012 (EP) .................................... 12001226

(51) Int. Cl.
| | | |
|---|---|---|
| *G01N 21/15* | (2006.01) | |
| *G01N 21/55* | (2014.01) | |
| *G01N 21/59* | (2006.01) | |
| *G01S 7/497* | (2006.01) | |
| *G01S 17/06* | (2006.01) | |
| *G01S 17/02* | (2006.01) | |

(52) U.S. Cl.
CPC ................ *G01N 21/15* (2013.01); *G01N 21/59* (2013.01); *G01S 7/497* (2013.01); *G01S 17/06* (2013.01); *G01S 17/026* (2013.01); *G01S 2007/4975* (2013.01); *G01N 21/55* (2013.01)
USPC ............................. 356/432; 356/445; 356/614

(58) Field of Classification Search
USPC .................. 356/432–440, 445–448, 601–623
See application file for complete search history.

(56) References Cited

U.S. PATENT DOCUMENTS

| | | | |
|---|---|---|---|
| 5,023,053 A * | 6/1991 | Finlan ........................ | 422/82.05 |
| 5,455,669 A | 10/1995 | Wetteborn | |
| 6,812,450 B2 | 11/2004 | Hipp | |
| 6,999,174 B2 * | 2/2006 | Amonette et al. ............ | 356/432 |
| 7,570,361 B2 | 8/2009 | Schneider et al. | |
| 2009/0212235 A1* | 8/2009 | Patt ........................... | 250/459.1 |
| 2012/0218564 A1 | 8/2012 | Wustefeld et al. | |
| 2013/0221207 A1* | 8/2013 | Wustefeld et al. ............ | 250/216 |

FOREIGN PATENT DOCUMENTS

| | | |
|---|---|---|
| DE | 39 08 273 C1 | 5/1990 |
| DE | 43 45 448 C2 | 7/1998 |
| DE | 197 32 776 C1 | 2/1999 |
| DE | 100 25 511 C1 | 12/2001 |
| DE | 198 00 968 C2 | 10/2002 |
| DE | 103 13 194 B4 | 7/2006 |

(Continued)

OTHER PUBLICATIONS

European Search Report cited in European Application No. EP12001226 dated Aug. 9, 2012. English translation is attached.

*Primary Examiner* — Hoa Pham

(74) *Attorney, Agent, or Firm* — Nath, Goldberg & Meyer; Jerald L. Meyer

(57) ABSTRACT

The invention relates to an optical sensor for monitoring a monitored zone having a detection device for observing a detection zone including the monitored zone, said detection device including a transmission device for transmitting transmission light into the detection zone and a receiver for receiving light reflected back or remitted back from the detection zone or transmitted through the detection zone and having at least one test object within the detection zone of the optical sensor. In accordance with the invention, the optical sensor has a device for avoiding and/or eliminating the contamination of the at least on test object.

22 Claims, 3 Drawing Sheets

(56) References Cited

FOREIGN PATENT DOCUMENTS

| | | |
|---|---|---|
| EP | 1 239 301 A1 | 9/2002 |
| EP | 1 308 747 A2 | 5/2003 |
| EP | 2 003 471 A1 | 12/2008 |
| EP | 2 053 538 A1 | 4/2009 |
| EP | 1 980 871 B1 | 6/2009 |
| EP | 2 394 882 A1 | 12/2011 |
| GB | 1 247 666 | 9/1971 |

* cited by examiner

OPTICAL SENSOR

FIELD OF INVENTION

The invention relates to an optical sensor for monitoring a monitored zone having a detection device for observing a detection zone including the monitored zone, said detection device including a transmission device for transmitting transmission light in the detection zone and a receiver for receiving light reflected back or remitted back from the detection zone or transmitted through the detection zone and having at least one test object within the detection zone of the optical sensor.

BACKGROUND INFORMATION

Known optical sensors e.g. include a transmission unit for transmitting transmission light into a detection zone, a receiver for receiving light reflected back or remitted back from the detection zone and an evaluation unit for evaluating the light reflected back or remitted back. In this respect, it can e.g. be a question of scanner systems in which a light beam produced e.g. by a laser is deflected via a light deflection unit into a detection zone and is there reflected or remitted by an object which may be present. The reflected or remitted light moves back to the scanner again and is detected by a receiver there. The light deflection unit is frequently designed to be pivotable or rotatable such that the light beam produced by the laser sweeps over the detection zone produced by the pivot movement. If a reflected or remitted light signal received by the receiver is received, a conclusion can be drawn on the angular position of the object in the detection zone from the angular position of the deflection unit.

Other optical sensors are configured as distance-measuring sensors which can draw a conclusion on the distance of the object e.g. from the light duration which a light signal irradiated into a detection zone requires back to the sensor again after reflection at an object in the detection zone.

A combination of such a scanner system and of a distance-measuring sensor can be used to completely monitor two-dimensional protected fields. A deflection in a further spatial direction while using a plurality of such scaners with e.g. protected fields arranged in fan shape or in parallel with one another also allows the monitoring of a three-dimensional space (3D scanners).

Such systems are used e.g. in driverless transport systems to avoid collisions. Other applications relate e.g. to machines in which a danger zone has to be monitored which may not be infringed by an operator in the operation of the machine. It can in this respect e.g. be a robot working zone. If the presence of an unpermitted object—that is, for example, a leg of an operator—is detected in the danger zone with the help of the laser scanner, an emergency stop of the machine is effected.

Such scanner systems are e.g. described in DE 39 08 273 C1 or EP 1 980 871 B1.

Other optical systems are configured as light barriers or as light gratings which detect the presence of an object in a detection zone by interrupting a light beam or by reflection of the light beam from the detection zone.

A monitoring of the most important performance functions is necessary for checking the operability, in particular for the reliable object detection and object localization in a safety system. In this respect, in known solutions, test objects are provided in the monitored zone of the sensor. A test is made before or during the measurement of whether these test objects are correctly detected. An optical sensor is known from DE 198 00 968 C2, wherein for this purpose a test object arranged in the interior of the sensor housing is illuminated through a corresponding inlet window. A scanner is known from DE 39 08 273 C1 in which the detection ability of the sensor can be monitored by monitoring the positions of a plurality of offset external test targets having defined degrees of reflection.

The long-term stability of the system is important. The use of safety scanners is therefore frequently in particular problematic in the outdoor sector since contamination or moisture precipitation at the test object can result in a reduction in the detection reliability, which can result in an unforeseeable defective response of the scanner.

SUMMARY OF THE INVENTION

It is the object of the present invention to provide an optical sensor which ensures a reliable measurement result and allows an increased long-term stability of the measurement.

This object is satisfied by an optical sensor having the features of claim 1. Preferred aspects are the subject of dependent claims.

In a sensor in accordance with the invention, a device is provided with which a contamination of the at least one test object can be avoided and/or eliminated.

The term "contamination" should in this respect include any form of foreign substances reaching the test object from the outside, that is e.g. also a moisture precipitation or similar.

It can be ensured in a reliable manner by such a device for avoiding and/or eliminating contamination of the at least one test object that such contaminants or other foreign substances cannot impair the correct detection of the test object. The long-term stability is thereby also ensured in surroundings which bear the risk of such contaminants, that is e.g. on a use outdoors. Such problems can, however, also generally occur in sensors which are not used outdoors if e.g. work is performed in an atmosphere prone to contamination.

A preferred embodiment of the optical sensor in accordance with the invention has a movement device for avoiding and/or eliminating contamination of the at least one test object and the test object can be moved with its aid. A possibly occurring contamination can thus already be effectively removed e.g. by vibration or fast rotation.

A particularly preferred embodiment provides an ultrasonic generator which applies ultrasound to the test object so that a cleaning effect arises. Alternatively, the test object can also be mounted on an ultrasound carrier which provides the described application of ultrasound to the test object.

A further embodiment provides that the optical sensor includes a housing, preferably a tube, which surrounds the at least one test object and which can serve in different manners for preventing and/or eliminating contaminants. Provision can thus be made in a particularly preferred embodiment that the housing has a ram pressure applied which keeps contaminating foreign substances away from the test object by the flow e.g. of air.

Another embodiment with a housing provides a front screen which is located at the housing on that side which is irradiated by the detection light of the optical sensor. With an otherwise closed housing, such a front screen effectively serves for the prevention of a contact of the test object with the environment and can e.g. easily be cleaned.

The optical sensor can e.g. have a movement device for moving the front screen or an ultrasonic generator for applying ultrasound to the front screen in order to clean the front screen. Other embodiments provide a mechanical cleaning apparatus for the front screen, e.g. a screen wiper.

Such a front screen is particularly advantageous if it is permeable for a wavelength or a wavelength range which is used by the transmission device. In this manner, the influence of environmental light on the quality of the test is ensured with the help of the test object and the influence of e.g. harmful UV light on the long-term stability of the test object is reduced.

If the front screen is arranged obliquely to the direction of the light incident on the test object from the transmission device, reflections of the transmission light are additionally prevented which could cause a falsification of the test object.

A further embodiment provides that the optical sensor has a device for rinsing the at least one test object with a liquid, e.g. water, or with a gas, e.g. air, which is used before or during the actual operation of the optical sensor for cleaning the test object.

To further increase the reproducibility and reliability of a system using test objects and to be able properly to utilize the advantages of the device for avoiding and/or eliminating contamination, a particularly advantageous embodiment of the at least one test object can in particular also be provided. A minimal degree of reflection which ensures the detection of the test object can e.g. be taken into account for the test object. The remission of the test object advantageously amounts to 2%. In this manner, the standard demands on minimal remission for person detection is ensured, in particular when the test target is positioned at a maximum distance of the respective programmed protected field.

Alternatively, the remission property or reflection property of the test object can e.g. be fixed such that it corresponds to a Class 3 reflector in accordance with the European Standard EN 471 and is likewise positioned at a maximum distance of the respective programmed protected field.

In other embodiments, in which the test object is arranged outside the monitored zone of the sensor, the test object advantageously has a degree of reflection or remission which corresponds to a multiple of a minimal degree of reflection or remission, preferably to a multiple of the above-addressed 2% remission, wherein the multiplication factor corresponds to the square of the ratio of the distance of the test object from the receiver and to the maximum extent of the monitored zone. Such a selection of the degree of reflection or remission of the test object takes the circumstance into account that the radiation intensity reduces with the square of the distance from the radiation source.

The size of the test target is advantageously selected such that it corresponds to the beam diameter of the transmission light or to the geometric resolution of the sensor. In this manner, the irradiated light is ideally used in the testing of the operability of the optical sensor.

If a plurality of test objects are used, they can be spatially offset from one another to ensure an ideal check of the operability of the sensor at different sites of the detection zone. This can be advantageous if different degrees of contamination have to be expected at different positions of the monitored zone.

On the other hand, it can e.g. be ensured by a spatial movement of the test object that it is exposed to different environmental conditions at different points in time so that a malfunction can be concluded from unexpected deviations and the measurement is not at risk in the total monitored zone by e.g. a particularly contamination-prone environment or particularly moist environment at a site of the monitored zone. In addition, with such an embodiment, the movement of the test object itself can be used to test the operability of the sensor if an expected movement of the test object (e.g. stored in a previous test run) is e.g. compared with the actually observed movement.

Finally, it is also possible that the test object itself is changed in another manner, e.g. in that it is rotated. Such a rotation serves, on the one hand, for the more effective removal of contaminants and can be utilized, on the other hand, additionally to test the operability of the sensor in that the measured rotational behavior is compared with an expected rotational behavior.

If the at least one test object is admittedly arranged in the detection zone, but outside the monitored zone, its detection is ensured even through it does not impede the monitoring of the monitored zone. On the other hand, it can be advantageous in corresponding applications if the at least one test object is arranged within the monitored zone to test the operability of the sensor with the aid of a test object which is located in exactly the same region in which objects which may have to be detected have to be detected.

The device in accordance with the invention for avoiding or eliminating contaminants of the test object can be used in different optical sensors. Distance-measuring sensors, scanning light gratings, two-dimensional and three-dimensional scanners or camera-based sensors are thus e.g. possible.

BRIEF DESCRIPTION OF THE DRAWINGS

The invention will be explained in detail with reference to the enclosed Figures which schematically show different embodiments and aspects of an optical sensor, but are not be understood as to scale. There are shown FIG. 1 a plan view of an optical sensor of an embodiment in accordance with the invention.

DETAILED DESCRIPTION

Figure 1:
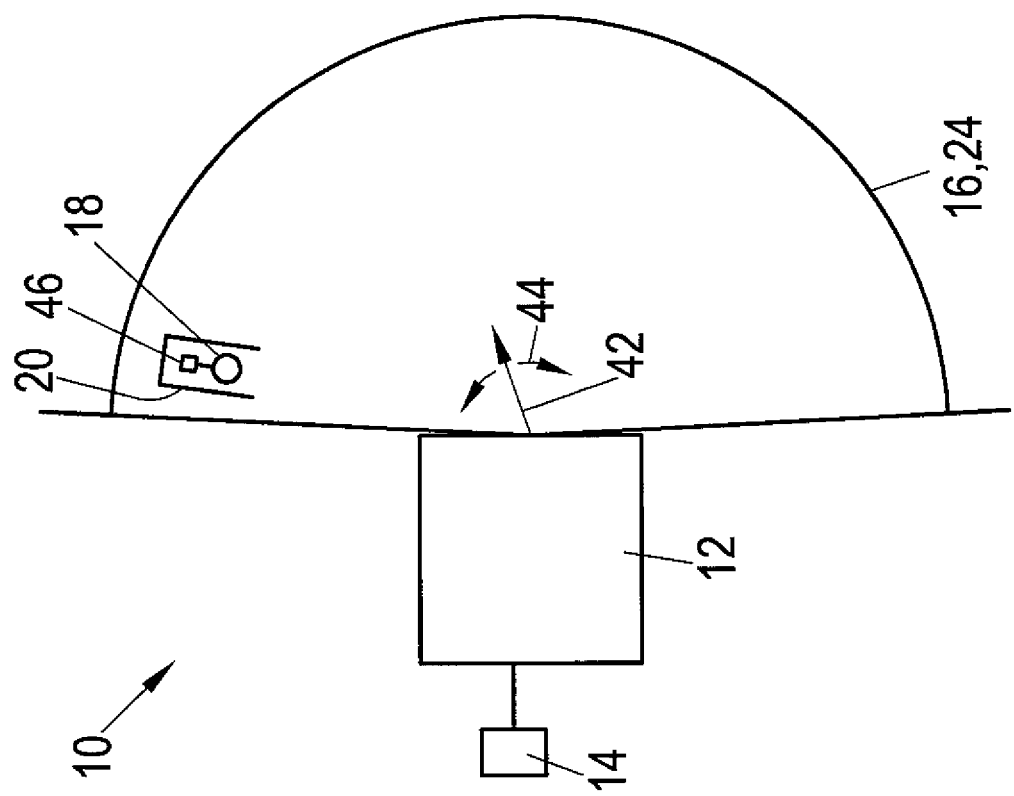

FIG. 1 shows the plan view of an optical sensor 10 with a detection device 12. The detection device in the present case includes an apparatus for transmitting transmission light 42 in a detection zone 24. The signals of the detection device 12 can be evaluated in the evaluation device 12. The light beam 42 is pivoted to and fro along the double arrow 44 with the aid of a deflection device in a manner known per se. If the light beam 42 is reflected e.g. by an object in the detection zone 24 during this pivot movement, it returns in the direction of the detection device 12 and is registered there in a manner known per se by a receiver, e.g. by a photodiode array. The distance of an object in the detection zone 24 can also be determined with the aid of the speed of light from the time of flight of light which the transmission light 42 requires from the transmission via the reflection to the incidence on the receiver.

The optical sensor 10 which is shown in the embodiment of FIG. 1 is accordingly a light sensor. The transmission light itself is produced e.g. with the aid of a laser.

The scanner 10 serves for monitoring a monitored zone 16. In the present example, this monitored zone 16 corresponds to the detection zone 24 which can be detected using the scanner 10.

The detection zone 24 is defined in this respect in that it corresponds to the maximum region which can be detected with the aid of the optical sensor 10. The correct determination of the distance of an object is therefore e.g. possible in the detection zone 24. Although this detection zone 24 does not necessarily have to coincide with the actually monitored zone 16, it is the case in the embodiment of FIG. 1.

A test object 18 is located in the detection zone 24. Its position is e.g. stored in a memory in the evaluation unit 14 so that on the sweeping over of the detection zone 24 by the transmission light 42, the position of the test object 18 can be determined as described and can then be compared with the expected position. It can be ensured in this manner that the optical sensor 10 works correctly. If e.g. the test object 18 is not detected at all or not at the expected site, a malfunction of the scanner is present, e.g. a defective light source or a defective receiver.

To be able to carry out this test reliably, it must be ensured that the reflectivity or remission of the test object 18 is largely unchanged. It is necessary for this purpose that the test object 18 is protected from contaminants and/or can be cleaned.

In the embodiment of FIG. 1, the test object 18 has a connection to an ultrasonic generator 46 for this purpose. For example, it can be mounted on an ultrasound carrier. A cleaning of the test object 18 is possible in an easy manner by the thus possible ultrasound treatment. In addition, it can be ensured by a continuous ultrasound treatment that contaminants does not adhere to the test object 18 at all.

In addition, the embodiment of FIG. 1 has a tube-like housing 20 which in particular protects the test object 18 at the side to prevent contamination entry from there.

Figure 3:
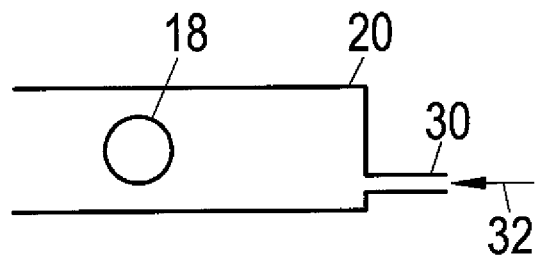
FIG. 3 a detail of a further embodiment in accordance with the invention.
Figure 4:
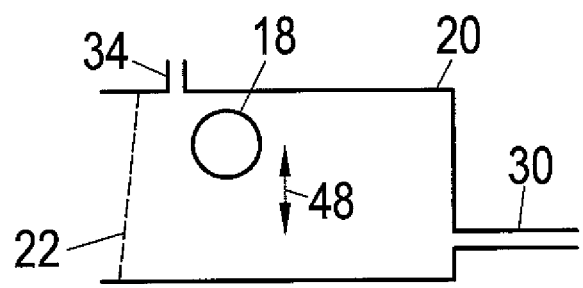
FIG. 4 a modification of this embodiment.

FIGS. 3 to 7 show by way of example other embodiments of how the test object can be configured. FIG. 3 e.g. shows an embodiment in which air 32 can be blown into the housing 20 through a supply passage 30 so that a kind of ram pressure is formed which keeps contaminants away from the test object 18. FIG. 4 shows an embodiment in which a front screen 22 is additionally provided which ends the test object 18 in the direction of the detection device 12. Such a front screen serves for the further contamination prevention of the test object 18. In the embodiment of FIG. 4, an outlet 34 is additionally shown through which the air ram pressure which is conducted through the passage 30 into the housing 20 can escape again.

FIG. 4 shows a further improvement of the system in which the test object 18 can be moved in the direction of the double arrow 48. This movement alone serves for the further prevention of possible contaminants. In addition, this movement can be utilized not only to be able to detect the presence of the test object, but also its movement. An even more precise monitoring of the scanner function is possible in this manner. The test object 18 can also be changed in another manner, e.g. can be configured as a light source and it can be checked by periodic switching on and off whether the scaners can determine this illumination change.

Figure 5:
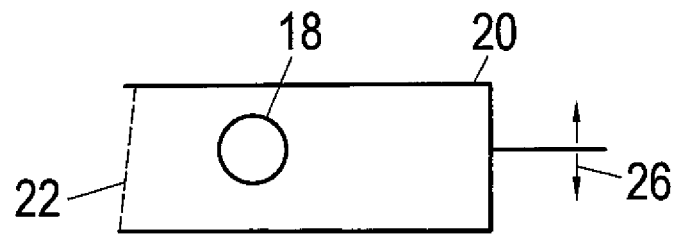
FIG. 5 a detail of a further embodiment in accordance with the invention.

FIG. 5 shows an embodiment in which the test object 18 is likewise accommodated in a closed housing 20 which is closed by a front screen 22. It is possible with the aid of a movement device 26 to move the total housing and therefore in particular to move the front screen 22, e.g. to set it into vibration, so that a contamination of the front screen 22 can be effectively prevented. Once the test object 18 is located within the housing 20, it is thus effectively prevented that the test object 18 is contaminated or that a contamination would influence the test measurement of the scanner.

Figure 6:
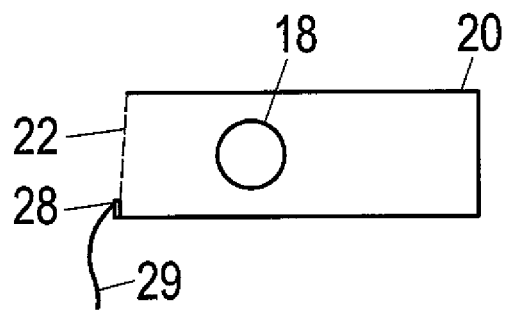
FIG. 6 a modification of such an embodiment.

FIG. 6 shows a similar aspect as that of FIG. 5, with here the front screen 22 being connected to an ultrasonic generator 28 (by a supply line 29) and being able to have ultrasound applied in this manner to ensure a cleaning of the front screen 22.

Figure 7:
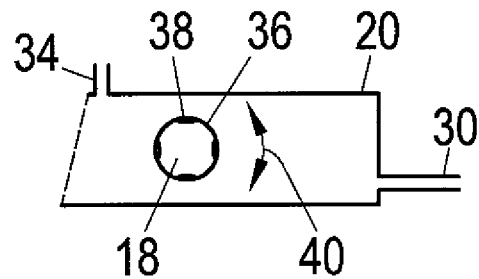
FIG. 7 a further modification of this embodiment.

FIG. 7 shows a modification of the aspect of FIG. 4 in which air can be conducted through the channel 30 through the housing 20 and the outlet 34 to keep the test object 18 clean. The test object 18 itself can be rotated in the direction of the double arrow 40. In the aspect shown, the test object 18 has different regions 36, 38 of different reflectivity. The regions 38 are thus e.g. darker than the regions 36. A periodically changing reflectivity pattern arises for the light beam 42 of the scanner 10 by the rotation in the direction of the double arrow 40 so that not only the presence of the test object can be detected by the scanner 10, but also a time change.

To prevent reflections of the light entering into the housing 20, the front screen 22 is e.g. arranged obliquely to the beam path. The front screen 22 is advantageously only permeable for the wavelength of the transmission light 42 so that the influence of environmental air on the quality of the test or the influence of UV light which may be harmful for the test object 18. is reduced.

The possibilities shown in the Figures of configuring a device with which a contamination of the test object can be prevented or eliminated can naturally be combined with one another in different manners without a combination having to be present which is also shown in the Figures. It is thus e.g. possible to use the ultrasonic generator 45 shown in FIGS. 1 and 2 in a system having a front screen 22 or additionally to provide an air ram pressure with the aid of a passage 30. In addition it is possible also to set a test object 18 into rotation which is moved with the aid of an ultrasonic generator 46 such as is explained by way of example of FIG. 7.

An embodiment which uses ram pressure for cleaning the test object 18 such as is e.g. shown in FIG. 4 can be combined with a front screen 22 which is provided in accordance with the aspect shown in FIG. 6 with a cleaning apparatus, here an ultrasonic generator 28, for cleaning the front screen. A movement of the housing 20 as is shown in FIG. 5 can naturally likewise be combined with other additional devices which are provided for eliminating or changing the contamination of the test target 18, that is e.g. the application of a ram pressure 32 through a passage 30. Corresponding arrangements can be combined as required and needed.

It is generally also possible that the test object is rinsed permanently by an airflow or a water flow to be able to remove contaminants immediately.

Figure 2:
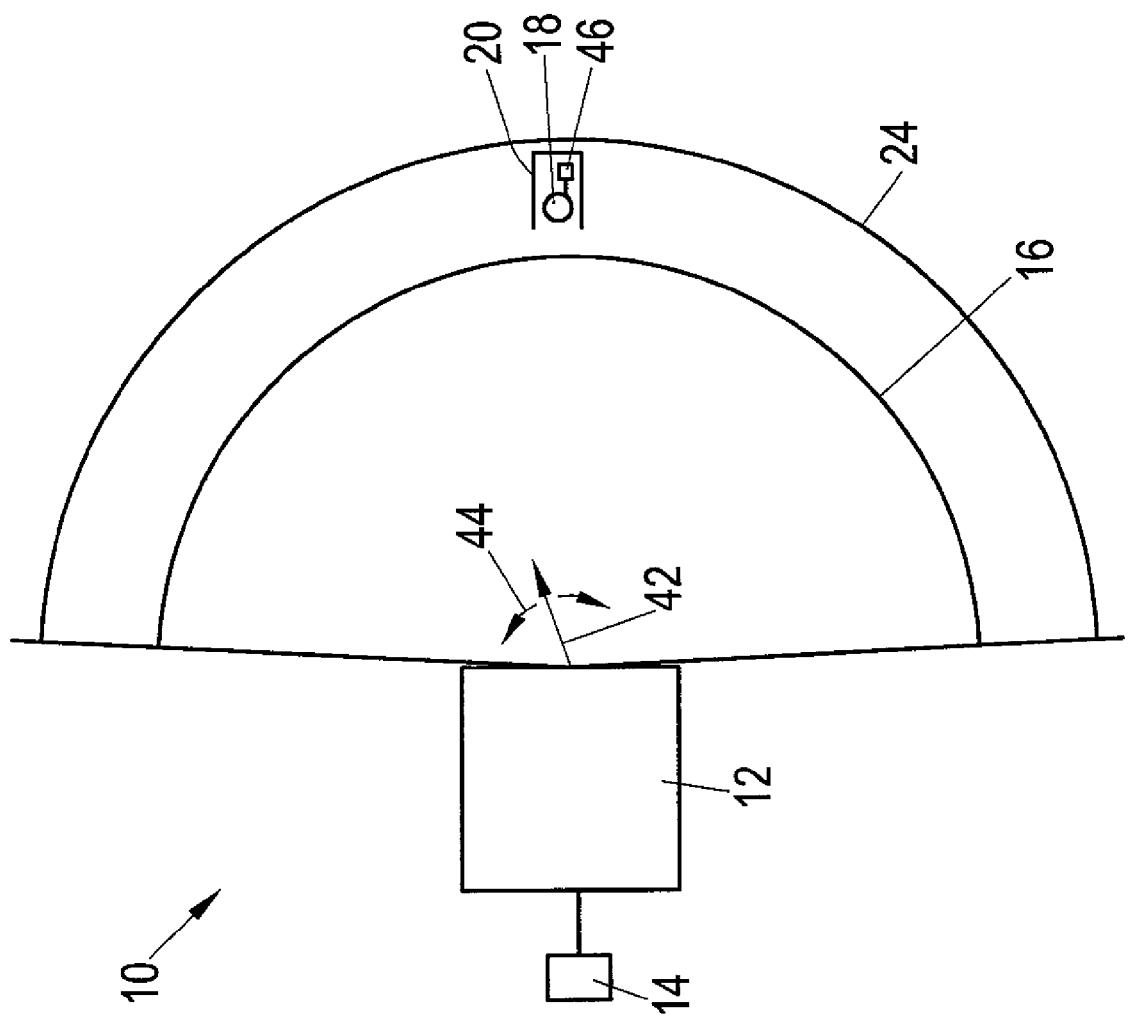
FIG. 2 a modification of the embodiment of FIG. 1.

An aspect is shown in FIG. 2 in which the detection zone 24 does not correspond to the monitored zone 16. In such an aspect, the optical sensor 10 is used for determining objects in the monitored zone 16. Since the detection zone 24, which can be reliably detected by the optical sensor 10, is, however, larger, an arrangement with a test object 18 can be located outside the monitored zone 16—but still inside the detection zone 24—such as was e.g. described in relation with FIG. 1. The corresponding arrangement is shown here only be way of example frontally opposite the detection device 12. What is decisive for this embodiment is that the test object 18 is admittedly outside the monitored zone 16—so that it does not impede a monitoring of this zone—but is inside the detection zone 24 to be able to be reliably detected to test the operability of the scanner 10.

The remission of the test object 18 can e.g. amount to 2% and thus correspond to the standard requirement on the minimal remission of person detection. If such a test object 18 is used at the margin of the monitored zone 16 remote from the detection device 12, it is thus ensured that a reliable detection of objects with a small remission of 2% is also still possible at the margin of the monitored zone 16.

In the embodiment of FIG. 2, the test object 18 is located outside the detection zone 16. Here, the remission can e.g. amount to a multiple of the named 2%, with the multiplication factor corresponding to the square of the relationship of the distance of the test object 18 from that of the detection device 12 and to the maximum extent of the monitored zone 16. The remission of a test object 18 located outside the protected zone 16 and scaled in this manner corresponds to a 2% remission of an object which is located directly at the outer margin of the monitored zone 16 (inverse square law).

The size of the test object 18 can advantageously be selected so that it at least corresponds to the beam diameter or to the geometric resolution of the optical sensor 16.

All the described aspects for the cleaning or preventing contamination of the test object 18 also serve in an advantageous manner for the long-term stability of the sensor 10.

The term "contamination" is used here for all those foreign strains on the test object which change the reflection or remission of the test object and can thus prevent the detection, such as dirt, moisture, precipitation, film, or the like.

REFERENCE NUMERAL LIST 10 optical sensor
12 detection device
14 evaluation device
16 monitored zone
18 test object
20 tube
22 front screen
24 detection zone
26 vibration device
28 ultrasonic generator
29 supply line
30 air passage
32 airflow
34 air outlet
36 bright region
38 dark region
40 rotary movement
42 transmission light
44 pivot movement
46 ultrasonic generator

The invention claimed is:

1. An optical sensor for monitoring a monitored zone, having
a detection device for observing a detection zone including the monitored zone, said detection device including a transmission device for transmitting transmission light into the detection zone and a receiver for receiving light reflected back or remitted back from the detection zone or transmitted through the detection zone; and
at least one test object within the detection zone of the optical sensor,
wherein the at least one test object has a degree of reflection or remission which corresponds to a multiple of a minimal degree of reflection or remission, wherein the multiplication factor corresponds to the square of the ratio of the distance of the test object from the detection device and to the maximum extent of the monitored zone, and wherein a device for avoiding or eliminating a contamination of the at least one test object is provided.

2. An optical sensor in accordance with claim 1, wherein a movement device for moving the at least one test object is provided.

3. An optical sensor in accordance with claim 2, wherein the movement device is an ultrasound generator.

4. An optical sensor in accordance with claim 1, wherein the device for avoiding or eliminating the contamination includes a housing surrounding the at least one test object.

5. An optical sensor in accordance with claim 4, wherein the housing is a tube.

6. An optical sensor in accordance with claim 4, wherein a device for applying a ram pressure to the interior of the housing is provided.

7. An optical sensor in accordance with claim 6, wherein the ram pressure is a ram air pressure.

8. An optical sensor in accordance with claim 6, wherein the housing is closed and includes a front screen at at least one side.

9. An optical sensor in accordance with claim 8, wherein the front screen is connected to a movement device for moving at least the front screen or to an ultrasonic generator for applying ultrasound to the front screen.

10. An optical sensor in accordance with claim 8, wherein the front screen has a mechanical cleaning device.

11. An optical sensor in accordance with claim 10, wherein the cleaning device is a screen wiper.

12. An optical sensor in accordance with claim 8, wherein the front screen is only permeable for a wavelength or a wavelength range which is used by the transmission device.

13. An optical sensor in accordance with claim 8, wherein the front screen is arranged obliquely to the direction of the light incident from the transmission device onto the at least one test object.

14. An optical sensor in accordance with claim 1, wherein a device for rinsing the at least one test object with a liquid or with a gas is provided.

15. An optical sensor in accordance with claim 14, wherein the liquid is water.

16. An optical sensor in accordance with claim 14, wherein the gas is air.

17. An optical sensor in accordance with claim 1, wherein the at least one test object has a degree of reflection or remission of 2%.

18. An optical sensor in accordance with claim 1, wherein the multiple corresponds to a multiple of 2%.

19. An optical sensor in accordance with claim 1, wherein the at least one test object has a size which corresponds to the diameter of the transmission light beam at the position of the test object.

20. An optical sensor in accordance with claim 1, wherein more than one test object is used which test objects are offset from one another spatially.

21. An optical sensor in accordance with claim 1, wherein the at least one test object is changeable.

22. An optical sensor in accordance with claim 1, wherein the at least one test object is movable.

* * * * *